US005750728A

United States Patent [19]

Wagner et al.

[11] Patent Number: 5,750,728
[45] Date of Patent: May 12, 1998

[54] PROCESS FOR THE PREPARATION OF AROMATIC BROMOMETHYL COMPOUNDS

[75] Inventors: Adalbert Wagner, Hattersheim/Main; Heinz-Werner Kleemann, Bad Homburg; Dieter Regnat, Frankfurt am Main; Hans-Jerg Kleiner, Kronberg/Taunus, all of Germany

[73] Assignee: Clariant GmbH, Frankfurt, Germany

[21] Appl. No.: 763,877

[22] Filed: Dec. 11, 1996

Related U.S. Application Data

[63] Continuation of Ser. No. 142,022, Oct. 28, 1993, abandoned.

[30] Foreign Application Priority Data

Oct. 29, 1992 [DE] Germany ............... 42 36 476.0
Mar. 18, 1993 [DE] Germany ............... 43 08 562.8

[51] Int. Cl.$^6$ ............... C07D 333/56; C07D 333/52; C07C 22/04
[52] U.S. Cl. ............... 549/57; 549/49; 570/183
[58] Field of Search ............... 570/183; 549/57, 549/49, 58

[56] References Cited

U.S. PATENT DOCUMENTS 4,692,527  9/1987  Leininger et al. ............... 544/405
4,740,519  4/1988  Shroot et al. ............... 514/443
5,420,300  5/1995  Dormoy ............... 549/49

FOREIGN PATENT DOCUMENTS 0828545  1/1952  Germany.

OTHER PUBLICATIONS

McMurry, "Organic Chemistry", 2nd. Ed., (1988), pp. 553–554.
Morrison & Boyd, "Organic Chemistry", 4th Ed., (1983), pp. 641–643.
Korke et al, "Bromination of Methyl Groups Bonded to Aromatic Rings", CA 114:81213, (1991).
Vaccher, Claud et al Synthetic Communication, Bd. 23, Nr. 5, 1993, pp. 671–679.
Sugiura Tsuneyuki et al, SYNLETT, Bd. 6, Jun. 1992, Stuttgart De pp. 531–533.
"Bromination—Introducing Bromine Into An Organic Compound By Addition or Substitution", Rompps Chemie–Lexikon, Achte, neubearbeitete und erweiterte Auflage, Dr. Otto–Albrecht Neumuller, Franckh'sche Verlagshandlung, W. Keller and Co., Stuttgart, 1979, p. 521.

Primary Examiner—Deborah Lambkin
Attorney, Agent, or Firm—Connolly & Hutz

[57] ABSTRACT

Aromatic bromomethyl compounds play a major role in the synthesis of active substances. They can be obtained in particularly pure form by the free-radical bromination of aromatic methyl compounds in the solvent chlorobenzene.

5 Claims, No Drawings

PROCESS FOR THE PREPARATION OF AROMATIC BROMOMETHYL COMPOUNDS

This is a continuation of application Ser. No. 08/142,022, filed Oct. 28, 1993, now abandoned which is herein incorporated by reference.

DESCRIPTION

Bromomethyl derivatives have long proved to be valuable intermediates for the preparation of catalysts and active substances, for example plant protection agents or pharmaceuticals. In general, aromatic bromomethyl compounds are obtained by free-radical bromination (see e.g. Römpps Chemielexikon (Römpps Chemical Encyclopedia), vol. 1, page 521, 8th edition (1979), Franckhsche Verlagshandlung Stuttgart).

Aromatic methyl compounds can be used as starting materials for the preparation of the corresponding aromatic bromomethyl compounds by free-radical bromination with brominating agents, e.g. N-bromosuccinimide or 1,3-dibromo-5,5-dimethylhydantoin, optionally with the addition of a free-radical initiator such as azoisobutyronitrile or benzoyl peroxide. This reaction is generally carried out using solvents, such as carbon tetrachloride, which are highly toxic and readily volatile as well.

The present invention provides a process for the preparation of aromatic bromomethyl compounds of formula (I):

$$A(CH_2-Br)_n \quad (I)$$

in which an aromatic compound $A(CH_3)_n$, (E), containing one or more methyl groups, is converted to the bromomethyl derivative of formula (I) in a free-radical bromination reaction using the solvent chlorobenzene, n being the number 1, 2 or 3, preferably 1 or 2.

$$A(CH_3)_n \xrightarrow[\text{chlorobenzene}]{[Br]} A(CH_2-Br)_n$$

Surprisingly, using chlorobenzene as the solvent makes it possible to improve the reaction yield. Furthermore, the lower toxicity of the solvent chlorobenzene affords simplifications in terms of process technology, which is advantageous especially for preparation in the pilot plant or on the production scale. Because of the high boiling point of chlorobenzene (132° C.), it is possible to optimize the reaction conditions over a relatively wide temperature range in industrial syntheses, depending on the reactivity of the educt.

The invention relates preferentially to a process for the preparation of those aromatic bromomethyl compounds of formula (I)

$$A(CH_2-Br)_n \quad (I)$$

in which n is the integer 1, 2 or 3, preferably 1 or 2, and the grouping A is a mono-, bi-, tri-, tetra-, penta- or hexacyclic aryl or heteroaryl radical optionally substituted by one, two, three or four substituents.

The grouping A can also be substituted by several —CH₃ groups, in which case all or only some of these are converted to CH₂—Br groups, depending on the amount of brominating agents used.

Aryl is preferably understood as meaning a $(C_6-C_{12})$-aryl radical, for example phenyl, naphthyl, biphenyl or binaphthyl, but especially phenyl or biphenyl.

The dibromination of a binaphthyl derivative containing two methyl groups is also preferred.

Heteroaryl is preferably understood as meaning $(C_1-C_9)$-heteroaryl groups which are derived from phenyl or naphthyl and in which one or more CH groups have been replaced with nitrogen and/or in which at least two adjacent CH groups have been replaced with a sulfur atom, an oxygen atom or an NH group to form a 5-membered aromatic ring. The following groupings are preferred heteroaryl groups:

furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, benzothienyl, pyridazopyridyl, pyridazopyrimidinyl, pyridinothienyl and imidazopyridyl.

Particularly preferred heteroaromatics are benzothiophen, pyridazopyridine, pyridazopyrimidine, thienyl, benzothiazole and pyridinothienyl.

Suitable substituents are basically all the conventional substituents of aromatic systems which are not themselves susceptible to free-radical bromination.

Examples of suitable substituents are halogen, especially F, Cl or Br, $-(CH_2)_m-COOR^1$, $-CONR^2$, $-SO_2NR^2$, $-SO_2R^3$, phenyl, phenyl mono- or di-substituted by halogen, $-CN$, $-(C_3-C_4)$-alkyl substituted by $COOR^1$ and $-(C_2-C_4)$-alkenyl substituted by $COOR^1$.

$R^1$ here is $(C_1-C_6)$-alkyl or hydrogen;

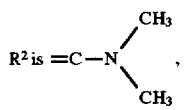

$R^3$ is $NHCOOR^1$; and m is an integer from 0 to 4, preferably 1 or 2.

As a rule, the yield of the bromomethyl compounds obtained by free-radical bromination using the solvent chlorobenzene is sufficiently high to obviate the need for further purification. Said compounds can then be used for the subsequent synthesis without expensive separation processes. If required, bromomethyl compounds can be obtained in particularly pure form by conventional methods such as chromatography, distillation or crystallization.

The reaction temperature in the process according to the invention (at normal pressure) is preferably between room temperature and the boiling point, especially from 60° to 132° C. In principle, the bromination can also be carried out under elevated pressure.

Conventional bromine-containing compounds can be used as brominating agents; N-bromosuccinimide has been found particularly suitable. The reaction time is between a few minutes and several hours, depending on the reactivity of the aromatic methyl compound used.

The invention will be illustrated in greater detail by the Examples which follow:

EXAMPLE 1

Process for the preparation of methyl 3-chloro-6-bromomethylbenzo[b]thiophen-2-carboxylate

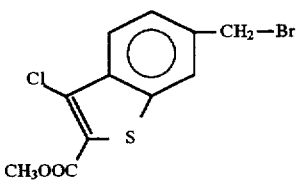

A mixture of 11 g (62 mmol) of NBS and 100 mg of benzoyl peroxide is added in portions, at the boiling point under reflux, to 15 g (62.5 mmol) of methyl 3- chloro-6-methylbenzo[b]thiophen-2-carboxylate in 100 ml of chlorobenzene. The solvent is evaporated off 30 minutes after the addition has ended. The remaining residue is taken up in 500 ml of ethyl acetate and washed once with each of 10% $Na_2SO_3$ solution, saturated $Na_2CO_3$ and saturated NaCl solution. This is followed by drying over $MgSO_4$ and concentration.

Yield: 19 g (88%).

The title compound is pure according to the thin layer chromatogram.

$R_f$(H/H1/4)=0.4. The product can be used without further purification for successive reactions, for example for the synthesis of active substances.

Even when the synthesis process is carried out on an appreciably larger scale, e.g. on the kilogram scale, it is possible to achieve a high product quality with a simple procedure.

The compounds according to Examples 2 to 32 below are obtained analogously.

| Ex. no. | A—$CH_2$—Br | MS ($M^+$ + H) | $R_f$ (eluent) |
|---|---|---|---|
| 2 | BrCH₂-benzothiophene-Cl, CN | 286 | 0.2 (E/H 1/4) |
| 3 | BrCH₂-benzothiophene-(CH₂)₂—CO₂CH₃, CO₂CH₃ | 371 | 0.6 (E/H 1/2) |
| 4 | BrCH₂-benzothiophene-CO₂CH₃ | 285 | 0.4 (E/H 1/2) |
| 5 | BrCH₂-benzothiophene-CH₂—CO₂C₂H₅ | 313 | 0.35 (E/H 1/4) |
| 6 | BrCH₂-benzothiophene-(CH₂)₂—CO₂CH₃ | 313 | 0.15 (E/H 4/1) |
| 7 | BrCH₂-benzothiophene-Cl, C(=O)—N=N(CH₃)₂ | 361 | 0.4 (E/H 1/1) |
| 8 | CH₂Br-C₆H₃(NO₂)(F) | 234 | distilled |
| 9 | CH₂Br-C₆H₄-CO₂CH₃ | 230 | 0.8 (E/H 2/1) |

-continued

| Ex. no. | A—CH₂—Br | MS (M⁺ + H) | R_f (eluent) |
|---|---|---|---|
| 10 | 5-CH₂Br, 2-(SO₂—N=CH—N(CH₃)CH₃), 1-H₃CO₂C substituted benzene | 363 | 0.35 (E) |
| 11 | 4-(CH₂Br)-C₆H₄-CH=CH-CO₂CH₃ | 253 | 0.5 (E/H 1/4) |
| 12 | 4-(CH₂Br)-C₆H₄-SO₂N=CH—N(CH₃)CH₃ | 305 | 0.3 (E/H 1/1) |
| 13 | 5-CH₂Br, 2-Br, 1-SO₂NHCO₂C₂H₅ substituted benzene | 400 | 0.4 (E/H/CH₃CO₂H 1/1 + 1%) |
| 14 | 4-(CH₂Br)-pyrimidine with N,N-C(CO₂C₂H₅)=C(phenyl) bridge | 360 | 0.3 (E/H 1/1) |
| 15 | 4-(CH₂Br)-pyridine with N,N-C(CO₂C₂H₅)=C(phenyl) bridge | 359 | 0.5 (E/H 1/1) |

-continued

| Ex. no. | A—CH₂—Br | MS (M⁺ + H) | R_f (eluent) |
|---|---|---|---|
| 16 | 4-(bromomethyl)pyridine-derived structure with CO₂C₂H₅ and CH₃ substituents | 297 | 0.4 (E/H 1/1) |
| 17 | pyridine with CH₂Br, NO₂, CO₂C₂H₅ and phenyl | 404 | 0.6 (E/H 1/1) |
| 18 | pyrazole (HN) with CH₂Br, CO₂C₂H₅ and phenyl | 348 | 0.6 (E/H 1/1) |
| 19 | pyrimidine with CH₂Br, CO₂C₂H₅ and 4-fluorophenyl | 378 | 0.35 (E/H 1/1) |
| 20 | pyridine with BrCH₂, CO₂C₂H₅ and 4-fluorophenyl | 377 | 0.3 (E/H 1/1) |

-continued

| Ex. no. | A—CH₂—Br | MS (M⁺ + H) | R_f (eluent) |
|---|---|---|---|
| 21 | (4-CH₂Br-pyridin-2-yl)imidazole with phenyl and CO₂C₂H₅ substituents | 359 | 0.25 (E/H 1/1) |
| 22 | (4-CH₂Br-pyridin-2-yl)imidazole with CO₂C₂H₅ and 4-fluorophenyl substituents | 377 | 0.3 (E/H/ 1/1) |
| 23 | (5-BrCH₂-pyridin-2-yl)imidazole with phenyl and CO₂C₂H₅ substituents | 359 | 0.3 (E/H 4/1) |
| 24 | (5-BrCH₂-pyridin-2-yl)imidazole with CO₂C₂H₅ and phenyl substituents | 359 | 0.3 (H/E 1/1) |
| 25 | 5-BrCH₂-thieno[2,3-b]pyridinone with CO₂C₂H₅ substituent | 326 | 0.3 (H/E 1/1) |
| 26 | (4-CH₂Br-pyridin-2-yl)imidazole with CN and phenyl substituents | 312 | 0.4 (E/H 1/1) |

-continued

| Ex. no. | A—CH₂—Br | MS (M⁺ + H) | R_f (eluent) |
|---|---|---|---|
| 27 | BrCH₂-(thiophene)-CH=C(CO₂CH₃)-phenyl | 337 | 0.4 (E/H 1/1) |
| 28 | 4-(BrCH₂)-C₆H₄-C(OH)(CO₂C₂H₆)-cyclohexyl | 356 | 0.15 (DIP/H 1/10) |
| 29 | 4'-(BrCH₂)-biphenyl-2-CO₂CH₃ | 306 | 0.15 (DIP/H 1/10) |
| 30 | 4'-(BrCH₂)-biphenyl-2-CN | 272 | 0.2 (DIP/H 1/1) |
| 31 | 4'-(BrCH₂)-biphenyl-2-N=CH-N(CH₃)₂ | 317 | 0.4 (E/H 1/1) |

| Ex. no. | A—CH₂—Br | MS (M⁺ + H) | R_f (eluent) |
|---|---|---|---|
| 32 | 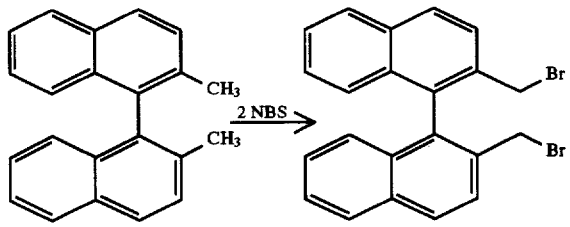 | 366 | 0.4 (DIP) |

Abbreviations:
H = n-heptane
E = ethyl acetate
DIP = diisopropyl ether
NBS = N-bromosuccinimide

EXAMPLE 33

The process for the preparation of 2,2'-bis(bromomethyl)-1,1'-binaphthyl is given as an example of a multiple bromination of methyl groups:

A mixture of 10.7 g (60 mmol) of N-bromosuccinimide and 100 mg of benzoyl peroxide is added in portions, at the boiling point under reflux, to 8.5 g (30 mmol) of 2,2-dimethyl-1,1'-binaphthyl in 100 ml of chlorobenzene. When the addition has ended, the resulting mixture is stirred for a further 1 hour at the boiling point and the solvent is evaporated off. The residue is taken up in 50 ml of ethyl acetate and washed once with each of 10% Na₂SO₃ solution, saturated Na₂CO₃ and saturated NaCl solution. This is followed by drying over MgSO₄ and concentration.

13.2 g (100%) of a yellow oil are obtained.

8.6 g of colorless crystals melting at 147°–149° C. crystallize from toluene.

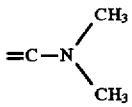

What is claimed is:

1. A process for the preparation of 2,2'-bis-(bromomethyl)-1,1'-binaphthyl which comprises treating 2,2-dimethyl-1,1'-binaphthyl dissolved in chlorobenzene with N-bromosuccinimide and obtaining 2,2'-bis-(bromomethyl)-1,1'-binaphthyl.

2. The process of claim 1 which is carried out using a free-radical initiator.

3. A process for the preparation of methyl 3-chloro-6-bromomethylbenzo[b]thiophene-2-carboxylate which comprises treating methyl 3-chloro-6-methylbenzo[b]thiophene-2-carboxylate dissolved in chlorobenzene with N-bromosuccinimide and obtaining methyl 3-chloro-6-bromomethylbenzo[b]thiophene-2-carboxylate.

4. The process of claim 3 which is carried out using a free radical initator.

5. A process for the preparation of an aromatic bromomethyl compound which comprises treating an aromatic methyl compound of the formula $$A(CH_3)_n$$

wherein A is a binaphthyl system and n is 2 or A is a $(C_6-C_{12})$aryl or $(C_1-C_9)$heteroaryl, said aryls optionally substituted by one, two, three or four substituents selected from the group consisting of halogen, —(CH₂)ₘ—COOR¹, —CONR², —SO₂NR², —SO₂R³, phenyl, phenyl substituted by halogen, —CN, —(C₁-C₄)alkyl substituted by COOR¹ and (C₂-C₄)alkenyl substituted by COOR¹ wherein R¹ is (C₁-C₆)alkyl or hydrogen, R² is $$=C-N\begin{matrix}CH_3\\CH_3\end{matrix}$$

R³ is NHCOOR¹, and m is an integer from 0 to 4, and n is 1, 2 or 3, dissolved in chlorobenzene with N-bromosuccinimide and obtaining the corresponding aromatic bromomethyl compound of the formula $$A(CH_2Br)_n$$

wherein A and n are as defined above.

* * * * *